United States Patent [19]
Tracy et al.

[11] Patent Number: 5,789,371
[45] Date of Patent: Aug. 4, 1998

[54] AMPHOTERIC SURFACTANTS HAVING MULTIPLE HYDROPHOBIC AND HYDROPHILIC GROUPS

[75] Inventors: David James Tracy; Ruoxin Li; Jiang Yang, all of Plainsboro, N.J.

[73] Assignee: Rhodia Inc., Cranbury, N.J.

[21] Appl. No.: 847,951

[22] Filed: Apr. 22, 1997

[51] Int. Cl.$^6$ ............................................. C11D 1/10
[52] U.S. Cl. ..................... 510/490; 510/499; 554/104
[58] Field of Search ........................... 510/490, 499; 544/358; 554/104

[56] References Cited

U.S. PATENT DOCUMENTS

| | | | |
|---|---|---|---|
| 2,374,354 | 4/1945 | Kaplan | 260/309.6 |
| 2,524,218 | 10/1950 | Bersworth | 252/117 |
| 2,530,147 | 11/1950 | Bersworth | 260/404.5 |
| 2,532,391 | 12/1950 | Bersworth | 260/404.5 |
| 2,568,876 | 9/1951 | White | 106/14 |
| 2,574,537 | 11/1951 | DeGroote | 260/309.6 |
| 2,773,068 | 12/1956 | Mannheimer | 260/309.6 |
| 2,781,354 | 12/1957 | Mannheimer | 260/309.6 |
| 2,820,043 | 1/1958 | Rainey | 260/309.6 |
| 2,846,440 | 8/1958 | Hughes | 260/309.6 |
| 3,024,277 | 3/1962 | Hotten | 260/534 |
| 3,033,704 | 5/1962 | Sherrill | 117/47 |
| 3,095,373 | 6/1963 | Blomfield | 252/8.8 |
| 3,152,080 | 10/1964 | Stuart | 252/51.5 |
| 3,187,003 | 6/1965 | McBride | 260/309.6 |
| 3,244,724 | 4/1966 | Guttmann | 260/309.6 |
| 3,555,041 | 1/1971 | Katz | 260/309.6 |
| 3,578,697 | 5/1971 | Marans | 260/465.4 |
| 3,620,807 | 11/1971 | Murray | 117/66 |
| 3,629,104 | 12/1971 | Maddox | 252/8.55 E |
| 3,855,156 | 12/1974 | Marumo | 252/547 |
| 3,887,476 | 6/1975 | McConnell | 252/8.75 |
| 3,888,797 | 6/1975 | Marumo | 252/527 |
| 3,941,817 | 3/1976 | Chakrabarti | 252/527 |
| 3,954,647 | 5/1976 | Neros et al. | 260/404.5 |
| 4,511,368 | 4/1985 | Knapp | 44/53 |
| 4,705,843 | 11/1987 | Stammann et al. | 528/212 |
| 4,917,993 | 4/1990 | Mukunoki et al. | 430/523 |
| 5,160,450 | 11/1992 | Okahara et al. | 252/174.21 |
| 5,175,220 | 12/1992 | Burba et al. | 525/526 |
| 5,250,702 | 10/1993 | Kondo et al. | 548/542 |
| 5,288,873 | 2/1994 | Su et al. | 548/323.5 |
| 5,300,235 | 4/1994 | Clewlow et al. | 252/8.555 |
| 5,312,617 | 5/1994 | Unger et al. | 424/9 |
| 5,322,630 | 6/1994 | Williams et al. | 252/8.553 |
| 5,488,180 | 1/1996 | Jenkins et al. | 568/609 |
| 5,569,767 | 10/1996 | Uphues et al. | 548/352.1 |

FOREIGN PATENT DOCUMENTS

| | | |
|---|---|---|
| 208562 B | 7/1984 | Czechoslovakia . |
| 1078101 | 8/1967 | United Kingdom . |
| 1149140 | 4/1969 | United Kingdom . |
| 1503280 | 3/1978 | United Kingdom . |
| WO 96/01800 | 1/1996 | WIPO . |

OTHER PUBLICATIONS

H. Hidaka, H. Sei, T. Furuta, T. Ishikawa, Yukagaku, 1978, vol. 27, pp. 370–374 (with abstract), Jun. 1978.
S. Piekarski, A. Hochapfel, Oleagineux, 1960, vol. 15, pp. 709–712 (with abstract), Apr. 1960.
Gao, et al. JAOCS; 71; No. 7 (Jul. 1994) 771–776.
Fischer, et al. Tenside Surf. Det. 31 2 (1994) 99–108.
Geminis: A New Generation of Surfactants M. Rosen, Chem. Tech. (Mar., 1993) pp. 30–33.
Menger, et al. JACS; 115 No. 22 (1993) 10083–10090.
Menger, et al. J. Org. Chem. 58; No. 7 (1993) 1909–1916.
Rosen, et al. J. Coll.+Interface Sci; 157; (1993) 254–259.
M. Rosen, et al. JAOCS 69; No. 1 (Jan. 1992).
Zhu, et al. JAOCS 69; No. 7 (Jul. 1992) 626–632.
Stein, et al. JACS 114; No. 10 (1992) 3943–3950.
Masuyama, et al; Yukagaku 41; No. 4 (1992) 301–305.
Zhu, et al. JAOCS 68; No. 4 (Apr. 1991) 268–271.
Zhu, et al. JAOCS 68; No. 7 (Jul. 1991) 539–543.
Menger, et al. JACS 113 No. 4 (1991) 1451–1452.
Zhu, et al. J. Jpn. Oil Chem. Soc. 40 No. 6; (1991) 473–477.
Zhu, et al. JAOCS 67; No. 7 (Jul. 1990) 459–463.
Ikeda, et al; J. Coll+Interface Sci; 130; No. 1 (Jun. 1989) 290–292.
Okahara, et al. J. Jpn. Oil Chem. Soc. 37; No. 9 (1988) 746–748.
Devinsky, et al; J. Coll+Interface Chem. 105; No. 1 (May 1985) 235–239.
Parreira, et al. JAOCS 56; (Dec. 12, 1978) 1015–1021.
Hidaka, et al; Yukagaku 27; 6 (1978) 370–374 (Abstract).
Martell, et al. JACS (Dec. 1950) pp. 5357–5361.

*Primary Examiner*—Paul Lieberman
*Assistant Examiner*—John R. Hardee
*Attorney, Agent, or Firm*—John Daniel Wood; Craig M. Bell

[57] ABSTRACT

According to the invention, an improved class of amphoteric surfactants having improved surfactant properties charaterized as mild and environmentally benign has been provided comprising a compound of the general formula:

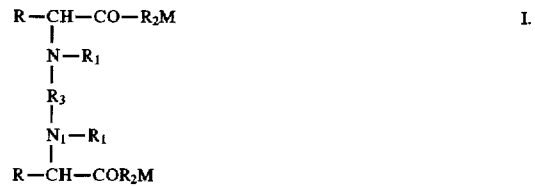

wherein R independently represents a $C_5$ to $C_{22}$ alkyl or acyl (RCO—); $R_1$ represents a $C_1$ to $C_6$ alkyl; $R_2$ independently represents —O—; $R_3$ represents a $C_2$ to $C_{20}$ alkylene, arylene, or alkylarylene and M is Na, K, $NH_4$, an organic base, or hydrogen.

In addition to the novel compounds per se, the invention also provides new methods for the preparation of the amphoteric gemini surfactants as well as improved synergistic compositions that are obtained when the amphoteric geminis are blended with other surfactants.

18 Claims, No Drawings

AMPHOTERIC SURFACTANTS HAVING MULTIPLE HYDROPHOBIC AND HYDROPHILIC GROUPS

This invention relates to a novel group of amphoteric surfactants having at least two hydrophobic moieties and at least two hydrophilic groups per molecule useful as emulsifiers, detergents, dispersants, hydrotropes, wetting agents, corrosion inhibitors and solubilizing agents.

BACKGROUND OF THE INVENTION

Surfactants are well known materials which can be generally described as having a hydrophobic moiety and a hydrophilic group per molecule. A wide variety of these materials are well known and are classified as anionic, cationic, nonionic and amphoteric. They are useful as emulsifiers, detergents, dispersants and solubilizing agents in the fields of cosmetics, textile treatment, industrial and personal cleaning preparations, corrosion inhibitors and the like.

In many surfactant containing compositions such as personal cleaning preparations, mildness is a sought after characteristic. The amphoteric surfactants are particularly important in fulfilling that need. Amphoteric surfactants are compounds uniquely structured to function as cationic surfactants at acid pH and anionic surfactants at alkaline pH. At neutral pH, the amphoteric surfactants are neutral, thus accounting for their mildness. Mildness is frequently associated with the critical micelle concentration (cmc) values of a surfactant. The lower the cmc, the fewer monomers are present in the solution. Amphoteric surfactants mollify the irritancy of anionic surfactants by lowering their cmc, thus reducing the free monomer concentration. Whereas a great deal of effort is being made in this area to produce new amphoteric surfactants with lower and lower cmc values, the gemini amphoteric surfactants of the present invention possess lower cmc values than conventional surfactants, thus enabling the development of even milder detergents and personal care products.

Amphoteric surfactants are well known in the art and are disclosed in U.S. Pat. Nos. 3,941,817 to Chakrabarti; 4,705,843 to Sotoya et. al.; and 2,781,354, and 2,773,068 to Mannheimer which are hereby incorporated by reference. Amphoteric surfactants are also known to be biodegradable and hence are ecologically benign.

U.S. Pat. No. 5,569,767 to Uphues et. al. teaches a class of storage stable ampholytic surfactants consisting of 1-hydroxyethyl-2-alkyl-2-imidazolidones which are quaternized or carboxymethylated with halogenated carboxylic acid salts at a pH of 7.5 to 9.0. The surfactants are asserted to be useful in dishwashing detergents, cosmetics and personal care products. 20 U.S. Pat. No. 5,288,873 to Su et. al. discloses a novel group of amphoteric surfactants comprising aminated alkoxylated imidazolidones, i.e., polyether diamines containing imidazolidones. The compounds are not gemini structures but are amphoteric surfactants useful in the curing and modification of multifunctional epoxy resins.

U.S. Pat. Nos. 5,175,220 and 5,175,219 to Burba et. al. discloses another class of amphoteric imidazoline compounds and methods for their preparation in which imidazolyl compounds are reacted with glycidyl ethers and acrylic acid to yield the amphoteric product. Again, the surfactants are not a gemini structure comprised of two hydrophilic and two hydrophobic moieties and are disclosed as useful as curing agents in epoxy resin compositions.

U.S. Pat. No. 3,629,014 to Maddox discloses another class of amphoteric surfactants consisting of the reaction products of aliphatic saturated mono- or dicarboxylic acids with substituted imidazolines to produce the imidazoline-aliphatic acid salts. Again, the amphoteric compounds do not possess the gemini two-head/two-tail structure but are shown to be useful in corrosion inhibitor compositions.

Whereas there are a wide variety of standard amphoteric surfactant compositions known in the art that are useful in a wide variety of applications, the amphoteric gemini surfactants are relatively unknown. This class of compounds with its dual hydrophilic/hydrophobic tails exhibit superior surface active functionality with improved foaming and emulsion characteristics while at the same time being mild, non-toxic and environmentally benign.

Whereas surfactants generally are compounds having one hydrophilic group and one hydrophobic moiety, recently, a group of compounds having two hydrophobic moieties and two hydrophilic groups have been discovered. These have become known as "Gemini surfactants" in the literature (*Chemtech*, March 1993, pp.30–33 and *J. American Chemical Soc.*, 115, 10083–10090, 1993) and the references cited therein. Since their introduction, cationic and anionic "gemini surfactants" have been disclosed. Other surfactant compounds having two hydrophilic groups and two hydrophobic moieties have been disclosed but not referred to as Gemini surfactants.

Due to the need for new and more effective and efficient surfactants, as well as the need for mild surfactants which are biologically compatible in an ecologically sensitive environment, effort has been made to develop a new class of compounds which demonstrate improved surface-active properties that are further characterized as mild and environmentally benign.

SUMMARY OF THE INVENTION

According to the invention, an improved class of amphoteric surfactants having improved surface active properties characterized as mild and environmentally benign has been provided comprising compounds of the general formula:

wherein R independently represents a $C_5$ to $C_{22}$ alkyl or acyl (RCO—); $R_1$ represents a $C_1$ to $C_6$ alkyl or hydrogen; $R_2$ independently represents —O— or —N $(R_4)CH_2CH_2SO^-_3$ wherein $R_4$ represents a $C_1$ to $C_6$ alkyl, cycloalkyl or hydrogen; $R_3$ represents a $C_2$ to $C_{20}$ alkyl or aryl with the further stipulation that both $R_1$ and $R_3$ can be components of a heterocyclic ring and M is Na, K, $NH_4$, an organic base or hydrogen.

Preferably, the surfactants of the present invention comprise compounds of the following formula:

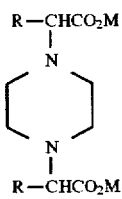  II.

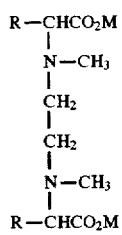  III.

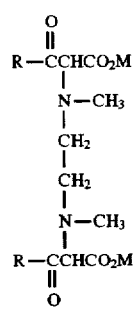  IV.

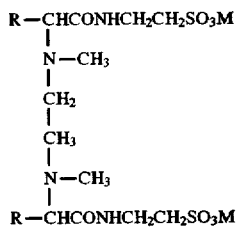  V.

wherein R and M are hereinbefore defined. Most preferably, R independently represents $C_{10}H_{21}$ alkyl while M is hydrogen.

When compared to the known, corresponding conventional amphoteric surfactants of the lauryl-amphopropionate and coco-amphosulfonate types, the novel compounds of the present invention show two unexpected surface active properties; unusually low critical micelle concentrations (cmc) and pC-20 values in aqueous media. These properties are a measure of the tendency of the surfactant to form micelles and adsorb at the interface respectfully, and consequently, to reduce surface tension.

The salts of Formula I can be an alkali metal salt (Na, K), an alkaline earth metal salt (Mg, Ca), an ammonium salt, or an organic base salt. The organic base salt can be illustrated by monoethanolamine, diethanolamine, triethanolamine, triethylamine, trimethylamine, N-hydroxyethyl morpholine and the like.

In addition to the novel compounds per se, the invention also provides new methods for the preparation of the amphoteric gemini surfactants as well as improved synergistic compositions that are obtained when the amphoteric geminis are blended with other surfactants.

DETAILED DESCRIPTION OF THE INVENTION

In the compounds of the above formula, R is derived from fatty acid triglycerides of natural or synthetic sources and generally will contain mixtures of different carbon chain length radicals within the chain length ranges defined above. R can be a mixture of saturated and unsaturated aliphatic radicals. The natural sources can be coconut oil or other similar natural oil sources such as palm kernel oil, palm oil, soya oil, rapeseed oil, castor oil or animal fat sources such as herring oil and beef tallow. Each R-group from these natural sources can be a mixture of alkyl radicals containing from about 5 to about 22 carbon atoms.

In a more preferred material, the mixture of alkyl radicals can be derived from a saturated portion of coconut oil or similar natural vegetable oil. In the case of coconut oil fatty acid, each R-group ranges from about 6 to about 18 carbon atoms. The ranges given cover about 90% of the preferred R-groups, i.e., carbon chains, in the compound. Since these R-groups are derived from natural sources, they will more than likely contain small amounts of other carbon chains. Illustrative of the fatty acids in these oils are caprylic ($C_8$), capric (10), lauric (12), myristic (14), palmitic (16), stearic (18), oleic (18, triunsaturated), ricinoleic (18, monounsaturated), arachidic (20), gadolic (20, monounsaturated), behenic (22) and erucic (22). These fatty acids can be used per se, as concentrated cuts or as fractionations of natural source acids. The even-numbered acids are the preferred source although the odd-numbered fatty acids can also be used. In addition, amphoteric surfactants based on single carboxylic acids such as lauric acid or other similar acids may be used depending on the particular application. Examples of useful acids derived from synthetic sources are 2-ethylhexanoic acid, pelargonic acid and the like.

In addition to the fatty acids which contain an active methylene that is in the alpha-position with respect to the carbonyl group, other species containing an active methylene can be used. For example, alkylnitriles, beta-ketoesters and beta-ketoacids can all be coupled utilizing the active methylene.

While the amphoteric surfactants of the present invention can be prepared by a variety of synthetic routes, the compounds can be produced particularly well by a novel process that utilizes carboxylic acids as the reactants and superior results are obtained when the carboxylic moiety is near the bridging group of the molecule. Useful coupling reagents include piperazine, ethylenediamine, diethylenetriamine, triethylenetetramine, N,N'-dimethylethyidiamine and mixtures thereof.

The surfactants can be prepared according to the following reaction sequence. First, the alpha-bromo methyl ester is prepared by treating the acid as follows:

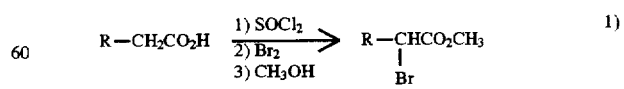  1)

whereby the acid is treated with thionyl chloride followed by bromine and methanol. The brominated acid methyl ester is then condensed with dimethylethylene diamine and hydrolyzed to yield the resulting gemini surfactant.

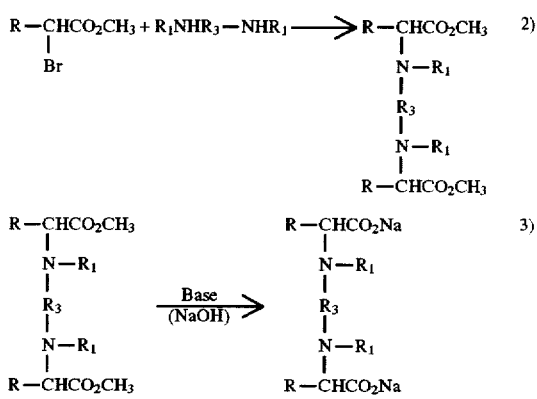 2)

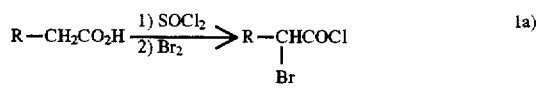 3)

Other amphoteric gemini surfactants can be prepared as follows wherein again, the respective acid is treated with thionyl chloride and bromine to yield the brominated acid chloride:

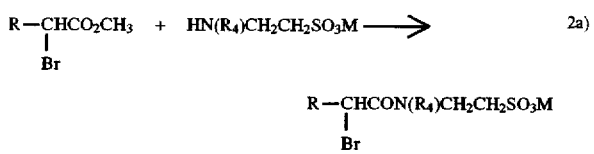 1a)

This is then condensed with an aminosulphonic acid as follows:

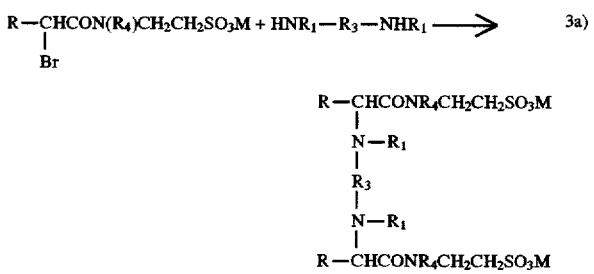 2a)

to produce the bromoamide intermediate. This, when combined with the desired diamine produces the corresponding gemini amphoteric surfactant.

3a)

Another amphoteric surfactant based on a beta-ketoacid can be made by the following sequence. A beta-ketoacid is reacted with thionyl chloride, brominated and converted to the alpha-bromoester. The ester is then reacted with a diamine and after hydrolysis, yields the gemini surfactant.

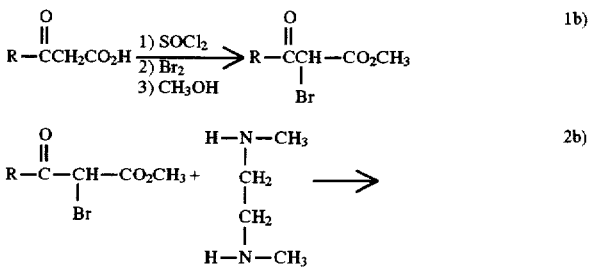 1b)

2b)

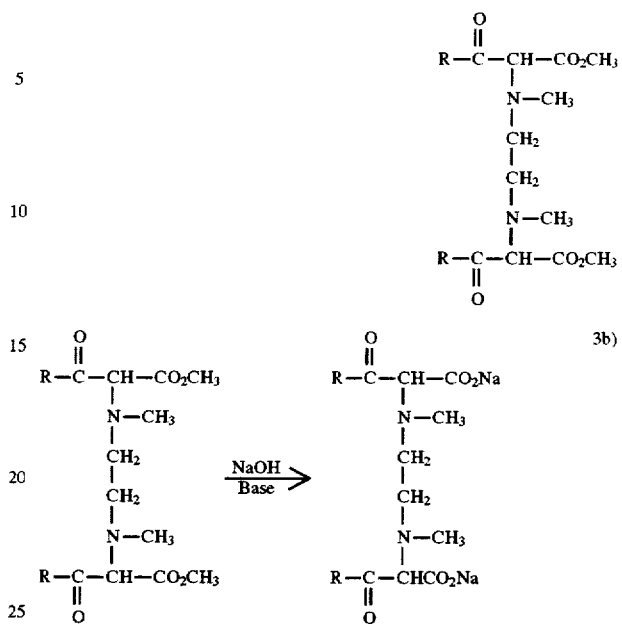

3b)

The surfactants of the invention exhibit superior foaming and surface active by functionalities and can be used alone as the essential hydrotrope component.

It has also been unexpectedly found that blends of the compounds of the invention as defined hereinbefore can be made with certain conventional well known anionic, nonionic, cationic and amphoteric surfactants that provide synergistic results that can be demonstrated in relation to critical micelle concentration and surface tension reducing ability.

Examples of the nonionic surfactants used herein include fatty acid glycerine esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethyiene alkyl amines, alkylpyrrolidones, glucamides, alkylpolyglucosides, mono- and dialkanol amides, polyoxyethylene alcohol mono- or diamides and alkylamine oxides.

Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives.

Examples of the cationic surfactants used herein include alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants. Examples of the amphoteric surfactants used herein include the amino acids, betaines, sultaines, phosphobetaines, imidazoline-type amphoteric surfactants, soybean phospholipids, and yolk lecithins.

In addition to the foregoing surfactants, any of the commonly used auxiliary additives may be added to the surfactants of the invention or blends thereof with other surfactants as disclosed herein. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

The amphoteric surfactants of the present invention exhibit greater surface tension reduction, lower toxicity, and excellent compatibility with other anionic, cationic and nonionic surfactants, and being extremely mild and non-irritating to both eyes and skin as well are adaptable for use in products ranging from cosmetics to industrial applications and are usable wherever amphoteric surfactants have found use.

These products are particularly useful in non-irritating shampoos including baby shampoos, body shampoos, including bubble baths, bar soaps, bath gels, hair conditioning gels, lotions, skin creams and lotions, make-up removal creams and lotions, liquid detergents, dish detergents and other washing and cosmetic products that contact the skin as well as bleach activators, bleach stabilizers and the like.

In addition, the compounds and compositions of the invention can be used in connection with hard surface cleaners, high electrolyte cleaners, emulsion polymerization, liquid and bar soap, laundry and dish detergents, bottle washing, carpet shampoo, water-based lubricants, metal cleaning, wax softener, oil well drilling lubricants and the like.

The following examples are provided to specifically teach and define how to synthesize compounds of the amphoteric surfactants of the present invention. They are for illustrative purposes only and it is understood that there are many variables that can be altered or changed in the process parameters and starting materials that will result in compositions not contemplated therein. It is to be understood that to the extent any such changes do not materially alter the structure and/or function of the final product, they are considered as following within the spirit and scope of the invention as recited by the claims that follow.

Example 1.

Preparation of Piperazine Bislauric Acid

A. Preparation of α-Bromolauric Acid Methyl Ester

Lauric acid (637.6 g, 3.19 mol) and thionyl chloride (455.3 g, 3.83 mol) were mixed together at room temperature. The mixture solution was gently heated to 40° C. A large amount of hydrogen chloride gas was generated. After the reaction was stirred for three hours at 40° C., nitrogen was bubbled into the solution to remove any remaining or leftover HCl gas. Bromine (612.5 g, 3.83 mol) was then added to the reaction solution. The reaction continued to stir for another 16 hours at 50° C. During the last two hours of the reaction, the temperature was raised to 70° C. Excess bromine was evaporated by bubbling nitrogen into the liquid.

The α-bromolauric acid chloride intermediate obtained from the last step was then cooled to 0° C. in an ice/water bath. Excess methanol was added drop-wise to the solution. The temperature of the reaction solution was kept under 15° C. while adding additional methanol. The final crude product was washed with water twice and dried under vacuum. The yield of the reaction was about 95%.

B. Coupling and Hydrolysis

Piperazine (2.8 g) was dissolved in dry dimethyl formamide (DMF) at 50° C. Bromolauric acid methyl ester (24.1 g) [prepared in part A] and sodium carbonate (8 g) were added to the solution. The reaction was stirred at 94° C. for 12 hours under nitrogen. The reaction was then stopped by cooling to room temperature. The inorganic salt was separated out by filtration. The organic portion was distilled under reduced pressure at 180° C. The structure of the final product was established by both proton and carbon nuclear magnetic resonance (NMR) analysis. The weight of the product was about 14.5 g which comprised an 85% yield.

Piperazine bislauric acid methyl ester was then dissolved in isopropanol at room temperature. A small amount of 50% NaOH solution was added to the reaction mixture. The reaction was stirred overnight at 55° C. The reaction was then stopped by cooling down to room temperature and the pH of the solution was adjusted to 10. The crude product was extracted with n-butanol twice and the organic layer was then collected and the solvent was evaporated under reduced pressure. The remaining solid material was washed with ethanol again and dried under vacuum. Both $^1$H-NMR and $^{13}$C-NMR spectral analysis agreed with the expected structure of the final product. The yield of the reaction was about 95%.

Example 2

Preparation of N,N'-Dimethylethylene Diamine Bislauric Acid Sodium Salt

The (α-bromolauric acid methyl ester (30 g, 124.9 mmol) prepared in part A of example 1 and N,N'-dimethylethylene diamine (5 g, 56.7 mmol) were stirred in dry DMF in the presence of sodium carbonate. After stirring for 48 hours at 70° C., the reaction was stopped by cooling the system down to room temperature. The inorganic salt was separated by filtration, while the organic layer was subsequently collected and the solvent rotoevaporated under reduced pressure. The excess starting material was stripped out at 200° C. (external temperature) for about 40 minutes. The final product was taken for $^1$H-NMR and $^{13}$C-NMR analysis. The NMR results agreed with the expected structure of the product. The yield of the reaction was about 90%.

N,N'-dimethylethylene diamine bislauric acid methyl ester was dissolved in ethanol at room temperature. A small amount of 50% aqueous NaOH was added to the reaction mixture. The reaction was stirred overnight at 60° C., and was then stopped by cooling the system to room temperature. The crude product was extracted with n-butanol twice and the organic layer collected. The remaining solvent was evaporated under reduced pressure and the solid residue material was again dissolved in methanol. Trace inorganic salt was separated by filtration while the final product was obtained by evaporating the methanol under reduced pressure. Both $^1$H-NMR and $^{13}$C-NMR agree with the expected structure of the final product. The yield of the reaction was about 90%.

Example 3

Preparation of Xylenediamine Coupled Laurylamidotaurinate

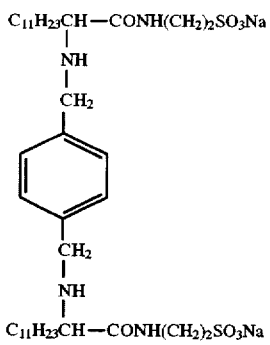

A. Preparation of Alpha Bromotaurinate

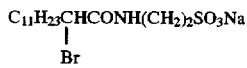

Lauric acid (637.6 g, 3.19 mol) and thionyl chloride (455.3 g, 3.83 mol) were mixed together at room temperature. The mixture solution was gently heated to 40° C. A large amount of hydrogen chloride gas was generated. After the reaction was stirred for three hours at 40° C., nitrogen was bubbled into the solution to remove any remaining or leftover HCl gas. Bromine (612.5 g, 3.83 mol) was then added to the reaction solution. The reaction continued to stir for another 16 hours at 50° C. During the last two hours of the reaction, the temperature was raised to 70° C. Excess bromine was evaporated by bubbling nitrogen into the liquid.

The α-bromolauric acid chloride intermediate was then cooled to room temperature.

Taurine (5 g) was dissolved in saturated sodium carbonate water solution (50 ml) at room temperature. α-bromoauric acid chloride (4.5 g) [prepared above] was then added drop-wise to the solution as it was stirred vigorously. During the adding process, the solution pH was kept at about 10 by adding additional saturated sodium carbonate solution. The mixture became white and sticky quickly. After stirring a few hours at room temperature, the reaction was stopped by extracted crude product from the water solution with n-butanol twice. Organic layer was collected and evaporated under reduced pressure. The final white powder product was dried under vacuum and taken for NMR analysis. The yield of the final product was 5.5 g. NMR results agree with the structure of the final product.

B. Xylenediamine Coupling

Alpha bromolauric taurine amide (6.0 g, 14.7 mmol) [prepared in part A] was dissolved in hot methanol. Xylylenediamine (1.0 g, 7.35 mmol) was then added to the solution. After the reaction was stirred for an hour at 60° C., sodium carbonate anhydrous (2.0 g) was added to the reaction solution. The reaction was refluxed overnight. Thin Layer Chromatography (TLC) [CHCl$_3$: CH$_3$OH: H$_2$O=3:1: trace] showed that there was a new UV active product formed. The reaction was stopped by separating inorganic salt with filtration. A hot methanol layer was collected and rotoevaporated under reduced pressure. The remaining solid material was dissolved in hot ethanol. The ethanol layer was then collected and evaporated. The final remaining light yellow solid material was dried under vacuum and taken for NMR study. NMR results agreed with the structure of the desired product. The yield of the reaction was about 70%.

Example 4

Surface Properties

The surfactants of the invention as prepared in examples 1 and 2 were measured for critical micelle concentration and surface tension reducing ability. The test methods utilized are described as follows:

Critical Micelle Concentration (cmc)

Aqueous solutions of the surfactants were prepared at varying concentrations. The surface tension at 20° C. was measured by the Wilhelmy plate method and plotted vs. the logarithm of the concentration. The critical micelle concentration (cmc) was determined as the value at which the slope of the line of the graph changed abruptly.

The surface tension reducing ability was determined from the surface tension at the critical micelle concentration.

Surface tension measurements were made for each of the surfactants prepared from examples 1 and 2 using a Kruss K-12 tensiometer (plate method). The appropriate values were determined as follows:

$$\rho = \frac{d\gamma}{d\log C_T} / 2.303RT$$

where

ρ=surface excess concentration (mol/cm$^2$)

γ=change in surface or interfacial tension of the solvent (dyn·cm$^-$)

R=8.31×10$^7$ erg mol$^{31}$ ·K$^1$

C=molar concentration of solution

T=absolute temperature (°K)

pC-20 at the solution/air interface is defined as the negative logarithm of the surfactant concentration required to lower surface tension by 20 dyne/cm.

Ross Miles Foam Height

The product was evaluated as a foaming agent using the Ross Miles Foam Height Test as outlined in ASTM method D1173 which is hereby incorporated by reference. The foam was evaluated and the results were recorded.

The results obtained for the surfactants alone are reported in Table 1.

TABLE 1

| Surfactant | Surface Tension (dyne/cm) | Critical Micelle Concentration (M) | Ross-Miles Foam Height (0.1%) (mm.) | PC$_{20}$ |
|---|---|---|---|---|
| Example 1 | 30.6 | 5.0 × 10$^{-5}$ | 155 → 90 | 5.7 |
| Example 2 | 25.1 | 3.8 × 10$^{-5}$ | 140 → 130 | 6.5 |

As can be seen from the respective derived values, the surfactants afford enhanced surface tension reduction properties.

When the surface properties for the amphoteric gemini surfactant compounds of the invention were compared to the corresponding conventional amphoteric surfactants, the novel compounds of the invention showed two unexpected surface active properties; unusually low critical micelle concentration cmc) and pC$_{20}$ values in aqueous media. These properties are a measure of the tendency of the surfactant to form micelles and adsorb at the interface, and consequently, to reduce surface tension respectively. This unusually high surface activity for these molecules is a result of their unique structure; the presence of two optimally spaced hydrophobic chains and hydrophilic groups.

This molecular structure of the surfactants of the present invention provide energetically favorable decreases in the free energy of adsorption and micellization through the favorable distortion of water structure while, at the same time, providing a "close packed" arrangement at the interface. This is a result of the surfactants relatively low surface area per molecule that is unexpected from the molecular dimensions for the molecule. The area per molecule for the compounds of the invention are comparable to corresponding conventional surfactants. The ability of the compounds of the invention to distort water structure through inhibition of crystalline or liquid crystalline phase formation in bulk phase and at the same time to pack closely on adsorption at the interface is contrary to conventional wisdom. This again demonstrates the uniqueness of the molecular design for these compounds which is very critical to providing unexpected exceptional surface and performance properties.

Exceptional surface activity and unique structural features for the compounds of the invention provide two other important performance properties that can have immense practical application in industry. These are their hydrotropicity, which is the ability of organic substances to increase the solubility of other insoluble organic substances in water, and their solubilization properties, i.e., their ability to dissolve water-insoluble organic compounds into aqueous surfactant solutions above their cmc levels. The compounds of the invention, because of their very low cmc values, are superior solubilizers. This latter property will not only allow the formulation of homogeneous water insoluble materials, but also will enhance the surface activity of other surfactants whose low water solubility restrict their use. These novel surfactants of the invention are far better than comparable conventional surfactants in hydrotroping and solubilizing properties.

Because of their unusually high surface activity, coupled with their hydrotropicity and solubilization properties, the compounds of this invention will provide exceptionally high performance properties, at very low concentration, in practical applications such as detergency emulsification, solubilization, dispersancy, hydrotropicity, foaming and wetting. In addition, due to their extremely low monomer concentration at use levels and because of their extremely low cmc values, the surfactants of the present invention can provide superior surface active functionalities when used in amount of from one to two orders less than the compounds of conventional surfactants and will thereby result in extremely low or no irritancy when used in personal care applications.

What we claim is:

1. A surfactant composition comprising a compound of the general formula:

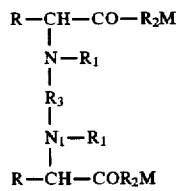

wherein R independently represents a $C_5$ to $C_{22}$ alkyl or acyl (RCO—); $R_1$ represents a $C_1$ to $C_6$ alkyl or hydrogen; $R_2$ independently represents —O—; $R_3$ represents a $C_2$ to $C_{20}$ alkylene, arylene, or alkylarylene and M may independently represent Na, K, $NH_4$, an organic base, or hydrogen.

2. The surfactant composition of claim 1 wherein said compounds are represented by the formula:

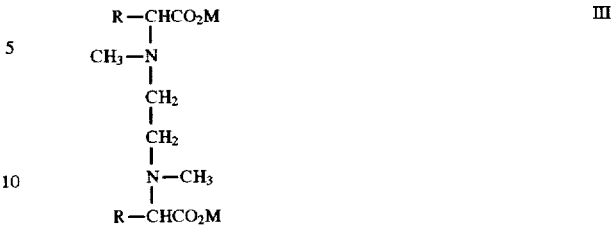

wherein R and M are herein before defined.

3. The surfactant composition of claim 1 wherein said compounds are represented by the formula:

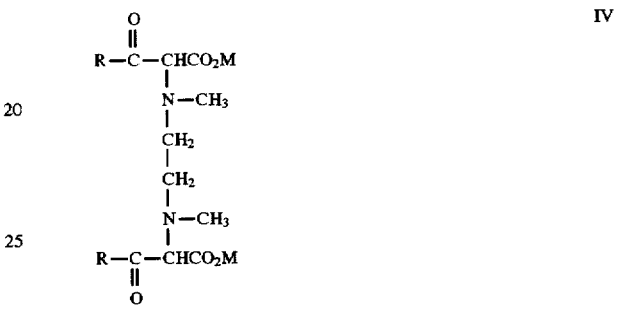

wherein R and M have been hereinbefore defined.

4. The surfactant composition of claim 2 wherein R is $C_{10}H_{21}$ and M is hydrogen.

5. The surfactant composition of claim 3 wherein R is $C_{10}H_{21}$ and M is hydrogen.

6. The surfactant composition of claim 1 wherein R is $C_{10}H_{21}$ and M is an alkali metal.

7. A blend of surfactants comprising a surfactant of the formula:

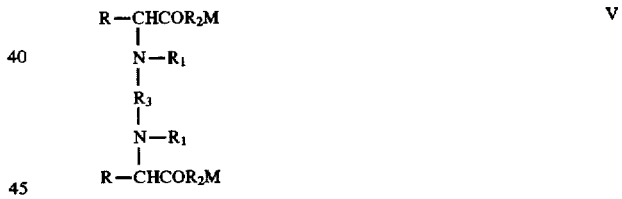

wherein R independently represents a $C_5$ to $C_{22}$ alkyl or acyl; $R_1$ represents a $C_1$ to $C_6$ alkyl or hydrogen; $R_2$ independently represents —O—; $R_3$ represents a $C_2$ to $C_{20}$ alkylene, arylene or alkylarylene and M may independently represent Na, K, $NH_4$, an organic base, or hydrogen and at least one surfactant selected from the group consisting of anionic surfactants, nonionic surfactants, cationic surfactants, amphoteric surfactants, zwitterionic surfactants and mixtures thereof.

8. The blend of surfactants of claim 7, wherein said nonionic surfactant is selected from the group consisting of fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxethylene lanolin alcohols, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oils or hardened castor oil derivatives, polyoxyethylene lanolin derivatives, polyoxethylene fatty acid amides, polyoxyethylene alkyl amines, alkyl pyrrolidones, glucamides,

13 alkylpolyglucosides, mono- or dialkanol amides, mono- or diamides, polyoxyethylene alcohols, alkylamine oxides and mixtures thereof.

9. The blend of surfactants of claim 7, wherein said anionic surfactant is selected from the group consisting of fatty acid soaps, ether carboxylic acids and the salts thereof, alkane sulfonate salts, α-olefin sulfonate salts, the sulfonate salts of a higher fatty acid ester, higher alcohol sulfate ester salts, fatty alcohol ether sulfate salts, higher alcohol phosphate ester salts, fatty alcohol ether phosphate ester salts, condensates of higher fatty acids and amino acids, collagen hydrolysate derivatives and mixtures thereof.

10. The blend of surfactants of claim 7, wherein said cationic surfactant is selected from the group consisting of alkyltrimethylammonium salts, dialkyl-dimethylammonium salts, alkyldimethylbenzylammonium salts, benzethonium chlorides, acylamino acid-type cationic surfactants and mixtures thereof.

11. The blend of surfactants of claim 7, wherein said amphoteric surfactant is selected from the group consisting of an amino acids, betaines, sultaines, phosphobetaines, imidazoline-type amphoteric surfactants, soybean phospholipids, yolk lecithins and mixtures thereof.

12. The surfactant of claim 7 further comprising an auxiliary additive.

13. The surfactant of claim 12, wherein said auxiliary additive is selected from the group consisting of an inorganic salt such as Glauber salt and common salt, a builder, a humectant, a solubilizing agent, a UV absorber, a softener, a chelating agent, a viscosity modifier and mixtures thereof.

14. A cleaning composition comprising an aqueous solution having a cleaningly effective amount of the composition of claim 7 dissolved therein.

15. The cleaning composition of claim 14, wherein the solution is selected from the group consisting of hair shampoos, baby shampoos, body shampoos, bubble baths, bar soaps, bath gels, hair conditioning gels, skin creams and lotions, skin contacting cosmetics, make-up removal creams and lotions, liquid detergents, dish detergents, liquid soaps, bleach activators, bleach stabilizers and the like.

16. The cleaning composition of claim 15, wherein the solution is selected from the group consisting of hard surface cleaners, emulsion polymerization activatives, laundry and dish detergents, liquid and bar soaps, carpet cleaners, lubricants, metal cleaners and textile processing acids.

17. A process for the preparation of novel gemini amphoteric surfactants of the general formula:

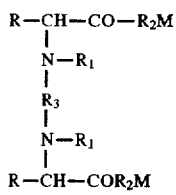

wherein R is a $C_2$ alkylene, $R_2$ independently represents O, $R_3$ independently represents a $C_7$ alkylene and M is hydrogen (a) treating an R-carboxylic acid with thionyl chloride in the presence of bromine and methanol to yield a brominated R-methyl ester intermediate; and (b) condensing said brominated R-methyl ester with dimethylethylenediamine followed by hydrolysis to yield the corresponding R-gemini amphoteric surfactant.

18. A surfactant composition comprising a compound of the general formula:

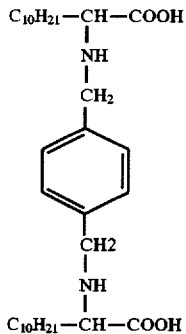

* * * * *